United States Patent
Iriyama et al.

(10) Patent No.: US 9,212,174 B2
(45) Date of Patent: Dec. 15, 2015

(54) CERTAIN β-DIHYDROFURAN DERIVATIVES

(75) Inventors: Yusuke Iriyama, Funabashi (JP); Tsutomu Higashiyama, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 272 days.

(21) Appl. No.: 13/579,004

(22) PCT Filed: Feb. 7, 2011

(86) PCT No.: PCT/JP2011/052508
§ 371 (c)(1),
(2), (4) Date: Aug. 14, 2012

(87) PCT Pub. No.: WO2011/099443
PCT Pub. Date: Aug. 18, 2011

(65) Prior Publication Data
US 2012/0322995 A1    Dec. 20, 2012

(30) Foreign Application Priority Data

Feb. 15, 2010  (JP) ................. 2010-030150
Dec. 3, 2010   (JP) ................. 2010-270835
Dec. 13, 2010  (JP) ................. 2010-277546

(51) Int. Cl.
C07D 307/32    (2006.01)
C07D 405/04    (2006.01)

(52) U.S. Cl.
CPC ............ *C07D 405/04* (2013.01); *C07D 307/32* (2013.01)

(58) Field of Classification Search
CPC ......... C07H 13/12; C07H 7/02; C07D 307/32
See application file for complete search history.

(56) References Cited

U.S. PATENT DOCUMENTS

| | | |
|---|---|---|
| 2004/0167096 A1 | 8/2004 | Cheng et al. |
| 2010/0280235 A1* | 11/2010 | Nagai et al. ............... 536/28.54 |
| 2011/0054164 A1 | 3/2011 | Sato et al. |

FOREIGN PATENT DOCUMENTS

| | | | |
|---|---|---|---|
| FR | 2781229 A1 | 1/2000 | |
| JP | 2-152976 A | 6/1990 | |
| JP | 5-501404 A | 3/1993 | |
| JP | 2003-504377 A | 2/2003 | |
| JP | 2006-528972 A | 12/2006 | |
| WO | WO 91/06554 A1 | 5/1991 | |
| WO | WO 99/29702 A2 | 6/1999 | |
| WO | WO 01/04134 A2 | 1/2001 | |
| WO | WO 2005/011709 A1 | 2/2005 | |
| WO | WO 2009/084655 A1 | 7/2009 | |
| WO | WO 2009/125841 A1 | 10/2009 | |

OTHER PUBLICATIONS

Greene et al., Protective Groups in Organic Synthesis, 1999, Third Edition, p. 17-245.*

Houlihan et al., Can. J. Chem., 1985, 63(1), p. 153-162.*

European Office Action for European Application No. 11742187.5 dated Feb. 10, 2014.

Wuts et al., "Carbonates," Protective Groups in Organic Synthesis, Fourth Edition, 2007, pp. 279-297.

Chen et al., "Synthesis of 3'-Fluoro-2',3'-dideoxy-2',3'-didehydro-4'-ethynyl-D- and -L-furanosyl Nucleosides," J. Org. Chem., vol. 69, No. 18, 2004, XP008137380, pp. 6034-6041.

Extended European Search Report for European Application No. 11742187.5, dated Jun. 6, 2013.

Hu et al., "One-Pot Synthesis of 5'-Diaryl Esters and Diamidates of Phosphate, Phosphorothioate, and Phosphoroselenoate Derivatives of AZT and d4T," Synthetic Communications: An International Journal for Rapid Communication . . . , vol. 39, No. 8, Mar. 19, 2009, pp. 1342-1354.

Mullah et al., "Potential Prodrug Derivatives of 2',3'-Didehydro-2',3'-dideoxynucleosides, Preparations and Antiviral Activities," J. Med. Chem., vol. 35, 1992, pp. 2728-2735.

Nguyen et al., "Deoxyuridine Triphosphate Nucleotidohydrolase as a Potential Antiparasitic Drug Target," J. Med. Chem., vol. 48, No. 19, 2005, pp. 5942-5954.

Sergheraert et al., "Synthesis and Anti-HIV Evaluation of D4T and D4T 5'-Monophosphate Prodrugs," J. Med. Chem., vol. 36, No. 7, 1993, XP-002311498, pp. 826-830.

Tortolani et al., "Prodrugs of 2',3'-Didehydro-3'-deoxythymidine (D4T): Synthesis, Antiviral Activity, and Rapid Pharmacokinetic Evaluation," Journal of Pharmaceutical Sciences, vol. 83, No. 3, Mar. 1994, pp. 339-343.

(Continued)

*Primary Examiner* — Jonathan S Lau
(74) *Attorney, Agent, or Firm* — Birch Stewart Kolasch & Birch, LLP

(57) ABSTRACT

The invention provides a process for producing a β-dihydrofuran derivative represented by formula (1) or a β-tetrahydrofuran derivative represented by formula (4), characterized in that the process includes causing a dialkyl dicarbonate, a diaralkyl dicarbonate, or a halide to act on a diol compound represented by formula (2) or (3). The invention also provides a process for producing 4'-ethynyl-2',3'-didehydro-3'-deoxythymidine or an analog thereof, the process including glycosylation and deprotection.

4 Claims, No Drawings

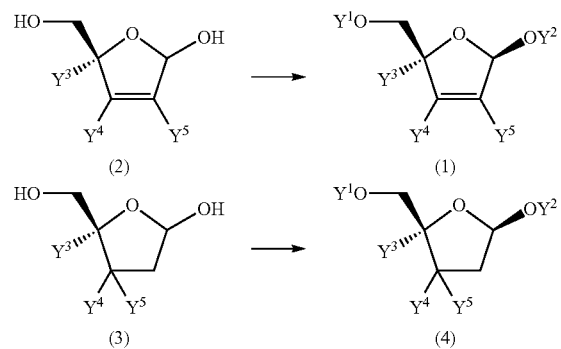

(56) References Cited

OTHER PUBLICATIONS

Bartlett et al., "Exploiting predisposition in the stereoselective synthesis of mono-, bi- and tetracyclic oxygen heterocycles: Equilibration between, and trapping of, alternative di- and tetraacetals," Org. Biomol. Chem., vol. 1, 2003, pp. 2393-2402.

Dupradeau et al., "Differential Solvation and Tautomer Stability of a Model Base Pair within the Minor and Major Grooves of DNA," J. Am. Chem. Soc., vol. 127, 2005, pp. 15612-15617.

Hegedus et al., "Asymmetric Synthesis of 4'-Ethoxy-2',3'-didehydro-2',3'-dideoxynucleosides by Palladium-Catalyzed Kinetic Discrimination between the Corresponding Diastereoisomeric Lactol Acetates," J. Org. Chem., vol. 67, 2002, pp. 4076-4080.

International Search Report for International Application No. PCT/JP2011/052508 dated Apr. 26, 2011.

Taverna-Porro et al., "Chemoenzymatic preparation of nucleosides from furanoses," Tetrahedron Letters, vol. 49, 2008, pp. 2642-2645.

Zhou et al., "Synthesis, Structure-Activity Relationships, and Drug Resistance of β-D-3'-Fluoro-2'3'-Unsaturated Nucleosides as Anti-HIV Agents," J. Med. Chem., vol. 47, 2004, pp. 3399-3408.

Brakta et al., "Palladium(0)-Based Approach to Functionalized C-Glycopyranosides," J. Org. Chem. (1989), vol. 54, pp. 1890-1896.

Hegedus et al., "Synthesis of 4'-Methyl and 4'-Cyano Carbocyclic 2',3'-Didehydro Nucleoside Analogues via 1,4-Addition to Substituted Cyclopentenones," J. Org. Chem. (2004), vol. 69, pp. 8492-8495.

Khan et al., "Pd(0) catalyzed intramolecular alkylation: stereoselective synthesis of furan and isoxazoline-2-oxide analogs," Tetrahedron (2007), vol. 63, pp. 1116-1126.

Saville-Stones et al., "Synthesis of (+)-2',3'-Didehydro-2',3'-dideoxy Nucleosides via a Modified Prins Reaction and Palladium (0) Catalysed Coupling," J. Chem. Soc. Perkin Trans 1 (1991), pp. 2603-2604.

* cited by examiner

CERTAIN β-DIHYDROFURAN DERIVATIVES

TECHNICAL FIELD

The present invention relates to a β-dihydrofuran derivative, to a process for producing a β-dihydrofuran derivative or a β-tetrahydrofuran derivative, to a β-glycoside compound, to a process for producing a β-glycoside compound, and to a process for producing a 4'-ethynyl-2',3'-didehydro-3'-deoxythymidine (i.e., 4'-ethynyl d4T) or an analog thereof.

BACKGROUND ART

Currently, pharmacotherapy of HIV infections is mainly carried out through a highly active anti-retroviral therapy (HAART), which is a multi-drug therapy employing a plurality of drugs in combination. HAART, however, has a downside in that replacement of one or more constituent drugs is unavoidable if and when a drug-resistant virus emerges or adverse side effects are observed. In order to solve this problem, a new active ingredient, 4'-ethynyl-2',3'-didehydro-3'-deoxythymidine (i.e., 4'-ethynyl d4T) was previously developed (see Patent Document 1). The compound 4'-ethynyl d4T is effective on multi-drug resistant virus and is considered to have low mitochondrial toxicity (i.e., high safety). From these points, this compound is expected to ensure long-term administration and maintenance of adherence.

In one known method for producing 4'-ethynyl d4T, thymidine or uridine is employed as a synthesis starting material (see Patent Document 1 and Non-Patent Document 1). This synthesis method, employing such a natural starting material, requires a number of synthesis steps, thereby elevates the production cost. Thus, the method is not suited for large-scale production, which is problematic.

In recent years, in order to overcome the drawback, another method for synthesizing 4'-ethynyl d4T employing inexpensive furfuryl alcohol serving as a starting material was developed, and this method requires relatively a small number of steps (see Patent Document 2). In this method, when a Lewis acid is used, α-form and β-form (43:53) are formed in the step of glycosylation (thymination) of a dihydrofuran compound. Thus, a subsequent separation/purification step considerably degrades the target yield, making the synthesis method unsuitable for mass production.

Meanwhile, in another known method for synthesizing a β-glycoside compound from a dihydrofuran compound, a palladium reagent is employed as a catalyst (see, for example, Non-Patent Document 2). Non-Patent Document 2 discloses that the method employs an achiral phosphine ligand and an α-β-mixed form dihydrofuran compound serving as a starting material, to thereby yield a product of an α-β-mixed form. The document also discloses that, when an optically active Trost ligand is used, only a β-glycoside compound is produced, and the starting α-form material is recovered. This clearly indicates that an α-form product is yielded from an α-form starting material, and a β-form product is yielded from a β-form starting material.

Through the aforementioned methods, a β-form-pure dihydrofuran compound must be synthesized and provided for attaining high-yield glycosylation.

Generally, methods for synthesizing a dihydrofuran compound are disclosed by several documents. In one disclosed method, a dihydrofurandiol compound corresponding to the target and serving as a starting material is diacetylized (see Patent Document 2). However, when the method is employed, the produced dihydrofuran compound has an α-β-mixed form (α:β or β:α=21:79), and no β-form-pure product is yielded.

There has also been reported a method for synthesizing a dihydrofuran compound in which a dihydrofurandiol compound having an asymmetric substituent serving as a starting material is silylated. However, the yielded dihydrofuran compound has an α-β-mixed form (α:β or β:α=80:20) (see Non-Patent Document 3).

Also known is a similar synthesis method in which a corresponding lactone is reduced and then acetylated. However, the yielded dihydrofuran compound has an β-β-mixed form (α:β=1:1) (see Non-Patent Document 2).

In the synthesis of a tetrahydrofuran compound, β-form-selective synthesis is known to be difficult. In one case, the 1-position ol and the 5-position ol of a tetrahydrofuranthiol compound are modified by two steps. However, the product is indicated to have an α-β-mixed form (Non-Patent Document 4).

Through synthesis of a tetrahydrofuran compound from glyceraldehyde, the product is indicated to have an β-β-mixed form (α:β=2:1) (Non-Patent Document 5).

As described above, those skilled in the art know that difficulty is encountered in selectively yielding a β-dihydrofuran compound, a β-tetrahydrofuran compound, and a β-glycoside compound.

PRIOR ART DOCUMENTS

Patent Documents

Patent Document 1: Japanese Patent Application Laid-Open (kokai) No. 2006-528972
Patent Document 2: WO 2009/84655, pamphlet

Non-Patent Documents

Non-Patent Document 1: Yoshino, "The Journal of Therapy," Vol. 88, No. 12 (2006.12), p. 2903
Non-Patent Document 2: Journal of Organic Chemistry, Vol. 67, p. 4076 (2002)
Non-Patent Document 3: Organic and Biomolecular Chemistry, Vol. 1, p. 2393 (2003)
Non-Patent Document 4: Journal of the American Chemical Society, Vol. 127, p. 15612 (2005)
Non-Patent Document 5: Journal of Medicinal Chemistry, Vol. 47, p. 3399 (2004)

SUMMARY OF THE INVENTION

Problems to be Solved by the Invention

An object of the present invention is to provide a process for selectively synthesizing a β-form glycoside compound. Another object is to provide a process for producing 4'-ethynyl-2',3'-didehydro-3'-deoxythymidine (hereinafter may be referred to as "4'-ethynyl d4T") and an analog thereof, which process is based on the selective β-form glycoside compound production process and which realizes large-scale synthesis thereof at high efficiency.

Means for Solving the Problems

The present inventors have conducted extensive studies in order to attain the aforementioned objects, and have found that a β-form compound can be selectively produced at high yield through carbonating, carbamating, or phosphating the 5-hydroxyl group of a dihydrofurandiol compound or a tetrahydrofurandiol compound, which can be readily synthesized through various techniques. The inventors have also found that 4'-ethynyl d4T and an analog thereof can be effectively produced through the above production process. The present invention has been accomplished on the basis of these findings.

Accordingly, the present invention provides the following.

[1] A β-dihydrofuran derivative represented by formula (1):

[F1]

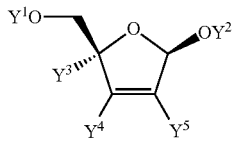
(1)

(wherein $Y^1$ represents an alkoxycarbonyl group, an aralkyloxycarbonyl group, an aminocarbonyl group, a dialkylphosphoryl group, or a diarylphosphoryl group; $Y^2$ represents an acyl group, an alkoxycarbonyl group, an aralkyloxycarbonyl group, an aminocarbonyl group, a dialkylphosphoryl group, or a diarylphosphoryl group; and $Y^3$, $Y^4$, and $Y^5$ each represent a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group, or an optionally substituted iminomethyl group).

[2] A process for producing a β-dihydrofuran derivative or a β-tetrahydrofuran derivative represented by formula (1):

[F3]

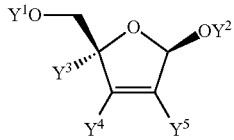
(1)

(wherein $Y^1$ represents an alkoxycarbonyl group, an aralkyloxycarbonyl group, an aminocarbonyl group, a dialkylphosphoryl group, or a diarylphosphoryl group; $Y^2$ represents an acyl group, an alkoxycarbonyl group, an aralkyloxycarbonyl group, an aminocarbonyl group, a dialkylphosphoryl group, or a diarylphosphoryl group; and $Y^3$, $Y^4$, and $Y^5$ each represent a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group, or an optionally substituted iminomethyl group) or formula (4):

[F4]

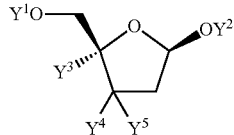
(4)

(wherein $Y^1$, $Y^2$, $Y^3$, $Y^4$, and $Y^5$ have the same meanings as defined in formula (1)), characterized in that the process comprises causing to act a dialkyl dicarbonate, a diaralkyl dicarbonate, or a halide on a diol compound represented by formula (2) or (3):

[F2]

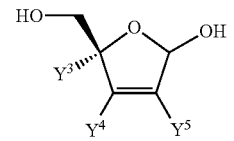
(2)

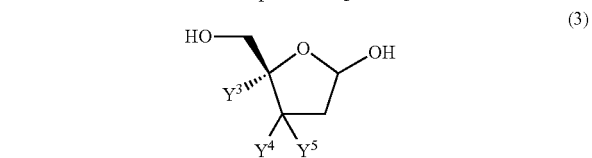
(3)

(wherein $Y^3$, $Y^4$, and $Y^5$ have the same meanings as defined in formula (1)).

[3] A β-glycoside compound represented by formula (5):

[F5]

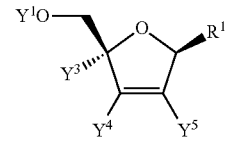
(5)

(wherein $Y^1$ represents an alkoxycarbonyl group, an aralkyloxycarbonyl group, an aminocarbonyl group, a dialkylphosphoryl group, or a diarylphosphoryl group; $Y^3$, $Y^4$, and $Y^5$ each represent a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group, or an optionally substituted iminomethyl group; and $R^1$ represents optionally substituted uracil-1-yl, optionally protected thymin-1-yl, optionally protected thymin-3-yl, optionally amino-protected cytosin-1-yl, imidazol-1-yl, benzimidazol-1-yl, benzo-1,2,3-triazol-1-yl, benzo-1,2,3-triazol-2-yl, optionally substituted thiouracil-1-yl, or optionally substituted purin-9-yl).

[4] A process for producing a β-glycoside compound represented by formula (5):

[F7]

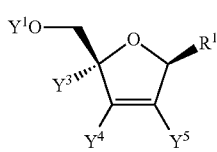

(5)

(wherein $Y^1$ represents an alkoxycarbonyl group, an aralkyloxycarbonyl group, an aminocarbonyl group, a dialkylphosphoryl group, or a diarylphosphoryl group; $Y^3$, $Y^4$, and $Y^5$ each represent a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group, or an optionally substituted iminomethyl group; and $R^1$ represents optionally substituted uracil-1-yl, optionally protected thymin-1-yl, optionally protected thymin-3-yl, optionally amino-protected cytosin-1-yl, benzimidazol-1-yl, benzo-1,2,3-triazol-1-yl, benzo-1,2,3-triazol-2-yl, optionally substituted thiouracil-1-yl, or optionally substituted purin-9-yl), characterized in that the process comprises causing, to react in the presence of a transition metal catalyst, a nucleophile selected from among optionally substituted uracil, optionally protected thymine, optionally amino-protected cytosine, imidazole, benzimidazole, benzo-1,2,3-triazole, optionally substituted thiouracil, and optionally substituted purine with a β-dihydrofuran derivative represented by formula (1):

[F6]

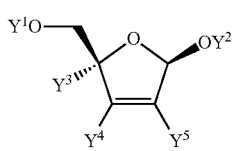

(1)

(wherein $Y^1$ represents an alkoxycarbonyl group, an aralkyloxycarbonyl group, an aminocarbonyl group, a dialkylphosphoryl group, or a diarylphosphoryl group; $Y^2$ represents an acyl group, an alkoxycarbonyl group, an aralkyloxycarbonyl group, an aminocarbonyl group, a dialkylphosphoryl group, or a diarylphosphoryl group; and $Y^3$, $Y^4$, and $Y^5$ each represent a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group, or an optionally substituted iminomethyl group).

[5] A process for producing 4'-ethynyl d4T or an analog thereof, characterized in that the process comprises deprotecting a β-glycoside compound represented by formula (5):

[F8]

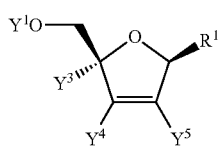

(5)

(wherein $Y^1$ represents an alkoxycarbonyl group, an aralkyloxycarbonyl group, an aminocarbonyl group, a dialkylphosphoryl group, or a diarylphosphoryl group; $Y^3$, $Y^4$, and $Y^5$ each represent a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group, or an optionally substituted iminomethyl group; and $R^1$ represents optionally substituted uracil-1-yl, optionally protected thymin-1-yl, optionally protected thymin-3-yl, optionally amino-protected cytosin-1-yl, imidazol-1-yl, benzimidazol-1-yl, benzo-1,2,3-triazol-1-yl, benzo-1,2,3-triazol-2-yl, optionally substituted thiouracil-1-yl, or optionally substituted purin-9-yl), to thereby produce a compound represented by formula (7):

[F9]

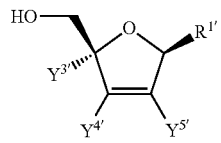

(7)

(wherein $Y^{3\prime}$ represents $Y^3$ in formula (5) or a residue formed by deprotecting $Y^3$, $Y^{4\prime}$ represents $Y^4$ in formula (5) or a residue formed by deprotecting $Y^4$, $Y^{5\prime}$ represents $Y^5$ in formula (5) or a residue formed by deprotecting $Y^5$, and $R^{1\prime}$ represents $R^1$ in formula (5) or a residue formed by deprotecting $R^1$).

[6] A β-dihydrofuran derivative as described in [1] above, wherein $Y^3$ is an optionally protected alkynyl group, and each of $Y^4$ and $Y^5$ is a hydrogen atom.

[7] A β-dihydrofuran derivative as described in [1] or [6] above, wherein each of $Y^1$ and $Y^2$ is an alkoxycarbonyl group.

[8] A β-glycoside compound as described in [3] above, wherein $Y^3$ is an optionally protected alkynyl group, each of $Y^4$ and $Y^5$ is a hydrogen atom, and $R^1$ is an optionally protected thymin-1-yl.

[9] A β-glycoside compound as described in [3] or [8] above, wherein $Y^1$ is an alkoxycarbonyl group.

[10] A process for producing a β-dihydrofuran derivative or a β-tetrahydrofuran derivative as described in [2] above, wherein $Y^3$ is an optionally protected alkynyl group, and each of $Y^4$ and $Y^5$ is a hydrogen atom.

[11] A process for producing a β-dihydrofuran derivative or a β-tetrahydrofuran derivative as described in [2] or [10] above, wherein each of $Y^1$ and $Y^2$ is an alkoxycarbonyl group.

[12] A process for producing a β-glycoside compound as described in [4] above, wherein $Y^3$ is an optionally protected alkynyl group, each of $Y^4$ and $Y^5$ is a hydrogen atom, and the nucleophile is thymine.

[13] A process for producing a β-glycoside compound as described in [4] or [12] above, wherein each of $Y^1$ and $Y^2$ is an alkoxycarbonyl group.

Effects of the Invention

According to the present invention, β-glycoside compounds can be selectively produced at high yield, whereby 4'-ethynyl d4T and analogs thereof can be more effectively produced on a large scale under milder conditions, as compared with currently employed processes. Since the compound 4'-ethynyl d4T is a candidate active ingredient of an effective drug for the treatment of HIV infections, the production process of the present invention is very useful for attaining the treatment in practice by use of the drug.

MODES FOR CARRYING OUT THE INVENTION

The present invention will next be described in detail.
Among the diol compounds represented by formula (2) or (3), serving as the starting materials of the production process of the present invention, the compound represented by formula (6):

[F10]

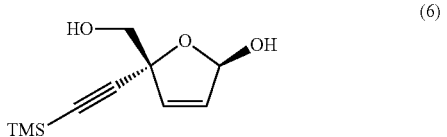

(6)

can be synthesized through a method disclosed in WO 2009/084655 (pamphlet) from 2-furylmethanol as a starting material. More specifically, the compound (6) may be produced according to, for example, the following reaction scheme. Notably, in the following scheme, N-bromosuccinimide is abbreviated as NBS, tetrahydrofuran as THF, sodium acetate as AcONa, acetic anhydride as Ac$_2$O, Lipase PS Amano SD (trade name, product of Amano Enzyme) as Lipase PS, isopropanol as IPA, trimethylsilyl as TMS, acetonitrile as MeCN, 4-dimethylaminopyridine as DMAP, and ethyl acetate as EtOAc.

[F11]

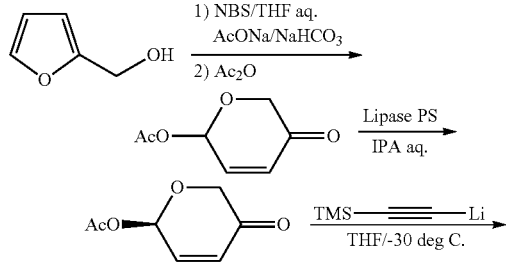

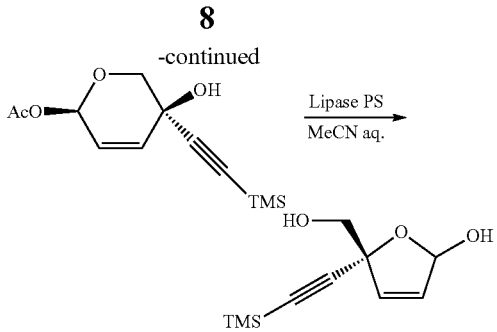

Generally, regarding the stereoisomerism of the dihydrofuran derivatives represented by formula (1), tetrahydrofuran derivatives represented by formula (4), glycoside compounds represented by formula (5), etc., an isomer having a substituent $OY^2$ or $R^1$ on the lower side of the sheet is called an α-form, and another isomer having a substituent $OY^2$ or $R^1$ on the upper side of the sheet is called a β-form, when the $OY^1$ is fixed on the upper side of the sheet.

Among the substituents ($Y^1$ and $Y^2$) which may be employed in the β-dihydrofuran derivatives represented by formula (1), diol compounds represented by formula (2) or (3), β-tetrahydrofuran derivatives represented by formula (4), and β-glycoside compounds represented by formula (5), the alkoxycarbonyl group may be linear-chain, branched, or cyclic. Examples of the alkoxycarbonyl group include methoxycarbonyl, ethoxycarbonyl, n-propoxycarbonyl, i-propoxycarbonyl, c-propoxycarbonyl, n-butoxycarbonyl, i-butoxycarbonyl, s-butoxycarbonyl, t-butoxycarbonyl, c-butoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, c-pentyloxycarbonyl, 2-methyl-c-butoxycarbonyl, n-hexyloxycarbonyl, 1-methyl-n-pentyloxycarbonyl, 2-methyl-n-pentyloxycarbonyl, 1,1-dimethyl-n-butoxycarbonyl, 1-ethyl-n-butoxycarbonyl, 1,1,2-trimethyl-n-propoxycarbonyl, c-hexyloxycarbonyl, 1-methyl-c-pentyloxycarbonyl, 1-ethyl-c-butoxycarbonyl, 1,2-dimethyl-c-butoxycarbonyl, n-heptyloxycarbonyl, n-octyloxycarbonyl, n-nonyloxycarbonyl, and n-decyloxycarbonyl. Of these, t-butoxycarbonyl is particularly preferred.

Among the substituents ($Y^1$ and $Y^2$), examples of the aralkyloxycarbonyl group include benzyloxycarbonyl, 1-phenethyloxycarbonyl, and 2-phenethyloxycarbonyl. Of these, benzyloxycarbonyl is particularly preferred.

Among the substituents ($Y^1$ and $Y^2$), the aminocarbonyl group may be linear-chain, branched, or cyclic. Examples of the aminocarbonyl group include methylaminocarbonyl, ethylaminocarbonyl, n-propylaminocarbonyl, i-propylaminocarbonyl, c-propylaminocarbonyl, n-butylaminocarbonyl, i-butylaminocarbonyl, s-butylaminocarbonyl, t-butylaminocarbonyl, c-butylaminocarbonyl, n-pentylaminocarbonyl, n-heptylaminocarbonyl, n-octylaminocarbonyl, n-nonylaminocarbonyl, n-decylaminocarbonyl, dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-c-butylaminocarbonyl, di-n-pentylaminocarbonyl, di-n-heptylaminocarbonyl, di-n-octylaminocarbonyl, di-n-nonylaminocarbonyl, di-n-decylaminocarbonyl, methylethylaminocarbonyl, methyl-n-propylaminocarbonyl, and methyl-n-butylaminocarbonyl. Of these, methylaminocarbonyl and t-butylaminocarbonyl are particularly preferred.

Among the substituents ($Y^1$ and $Y^2$), the dialkylphosphoryl group may be linear-chain, branched, or cyclic. Examples of the dialkylphosphoryl group include phosphoryl groups in which the R moiety of the phosphoryl group represented by (R—O)$_2$P(=O)— is an alkyl group. Specific examples include dimethylphosphoryl, diethylphosphoryl, di-n-propylphosphoryl, di-i-propylphosphoryl, di-c-propylphosphoryl, di-n-butylphosphoryl, di-i-butylphosphoryl, di-s-butylphosphoryl, di-t-butylphosphoryl, di-c-butylphosphoryl, di-n-pentylphosphoryl, di-(1-methyl-n-butyl)phosphoryl, di-(2-methyl-n-butyl)phosphoryl, di-(3-methyl-n-butyl) phosphoryl, di-(1,1-dimethyl-n-propyl)phosphoryl, di-c-pentylphosphoryl, di-(2-methyl-c-butyl)phosphoryl, di-n-hexylphosphoryl, di-(1-methyl-n-pentyl)phosphoryl, di-(2-methyl-n-pentyl)phosphoryl, di-(1,1-dimethyl-n-butyl) phosphoryl, di-(1-ethyl-n-butyl)phosphoryl, di-(1,1,2-trimethyl-n-propyl)phosphoryl, di-c-hexylphosphoryl, di-(1-methyl-c-pentyl)phosphoryl, di-(1-ethyl-c-butyl) phosphoryl, and di-(1,2-dimethyl-c-butyl)phosphoryl.

Among the substituents ($Y^1$ and $Y^2$), examples of the diarylphosphoryl group include phosphoryl groups in which the R moiety of the phosphoryl group represented by (R—O)$_2$P (=O)— is an aryl group. Specific examples include diphenylphosphoryl, di-o-methylphenylphosphoryl, di-m-methylphenylphosphoryl, di-p-methylphenylphosphoryl, di-o-trifluoromethylphenylphosphoryl, di-m-trifluoromethylphenylphosphoryl, di-p-trifluoromethylphenylphosphoryl, di-p-ethylphenylphosphoryl, di-p-i-propylphenylphosphoryl, di-p-t-butylphenylphosphoryl, di-o-chlorophenylphosphoryl, di-m-chlorophenylphosphoryl, di-p-chlorophenylphosphoryl, di-o-bromophenylphosphoryl, di-m-bromophenylphosphoryl, di-p-bromophenylphosphoryl, di-o-fluorophenylphosphoryl, di-p-fluorophenylphosphoryl, di-o-methoxyphenylphosphoryl, di-p-methoxyphenylphosphoryl, di-o-trifluoromethoxyphenylphosphoryl, di-p-trifluoromethoxyphenylphosphoryl, di-p-nitrophenylphosphoryl, di-p-cyanophenylphosphoryl, di-3,5-dimethylphenylphosphoryl, di-3,5-bistrifluoromethylphenylphosphoryl, di-3,5-dimethoxyphenylphosphoryl, di-3,5-bistrifluoromethoxyphenylphosphoryl, di-3,5-diethylphenylphosphoryl, di-3,5-di-i-propylphenylphosphoryl, di-3,5-dichlorophenylphosphoryl, di-3,5-dibromophenylphosphoryl, di-3,5-difluorophenylphosphoryl, di-3,5-dinitrophenylphosphoryl, di-3,5-dicyanophenylphosphoryl, di-2,4,6-trimethylphenylphosphoryl, di-2,4,6-tristrifluoromethylphenylphosphoryl, di-2,4,6-trimethoxyphenylphosphoryl, di-2,4,6-tristrifluoromethoxyphenylphosphoryl, di-2,4,6-trichlorophenylphosphoryl, di-2,4,6-tribromophenylphosphoryl, di-2,4,6-trifluorophenylphosphoryl, di-α-naphthylphosphoryl, di-β-naphthylphosphoryl, di-o-biphenylylphosphoryl, di-m-biphenylylphosphoryl, and di-p-biphenylylphosphoryl. Of these, diphenylphosphoryl is particularly preferred.

Among the substituents ($Y^2$), examples of the acyl group include formyl, acetyl, fluoroacetyl, difluoroacetyl, trifluoroacetyl, chloroacetyl, dichloroacetyl, trichloroacetyl, propionyl, pivaloyl, tigloyl, benzoyl, benzoylformyl, benzoylpropionyl, and phenylpropionyl.

No particular limitation is imposed on the substituent ($Y^3$, $Y^4$, or $Y^5$) which may be employed in the β-dihydrofuran derivatives represented by formula (1), diol compounds represented by formula (2) or (3), β-tetrahydrofuran derivatives represented by formula (4), and β-glycoside compounds represented by formula (5), and any substituents including a hydrogen atom may be employed. Examples of preferred substituents include a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group and an optionally substituted iminomethyl.

Examples of the $R^1$ which may be employed in the β-glycoside compounds represented by formula (5) include heterocyclic base substituents such as optionally substituted uracil-1-yl, optionally protected thymin-1-yl (e.g., 4-O-methylthymine-1-yl), optionally protected thymin-3-yl, optionally amino-protected cytosin-1-yl, imidazol-1-yl, benzimidazol-1-yl, benzo-1,2,3-triazol-1-yl, benzo-1,2,3-triazol-2-yl, optionally substituted thiouracil-1-yl, and optionally substituted purin-9-yl. Among them, optionally substituted uracil-1-yl, optionally protected thymin-1-yl, cytosin-1-yl, imidazol-1-yl, benzimidazol-1-yl, benzo-1,2,3-triazol-1-yl, optionally substituted thiouracil-1-yl, and optionally substituted purin-9-yl are preferred.

As used herein, the expression "optionally substituted" refers to that a hydrogen atom or hydrogen atoms are optionally substituted by one or more substituents, which are identical to or different from one another, selected from among a halogen atom, a C1 to C7 alkyl group, a C1 to C7 alkoxy group, a C6 to C12 aryl group, a carboxyl group, a C1 to C7 acyl group, a nitro group, and a cyano group.

Also, as used herein, the expression "optionally protected" refers to that a group is optionally protected by a protective group which is employed in general organic synthetic reaction.

Protective groups preferably in the reaction are as follows.

Examples of the protective group for a hydroxy group or a mercapto group include alkyl protective groups such as methyl, benzyl, p-methoxybenzyl, and t-butyl; acetal protective groups such as methoxymethyl, 2-tetrahydropyranyl, and ethoxyethyl; acyl protective groups such as acetyl, pivaloyl, and benzoyl; and silyl protective groups such as trimethylsilyl, triethylsilyl, t-butyldimethylsilyl, triisopropylsilyl, and t-butyldiphenylsilyl.

Examples of the amino-group-protective group include protective groups forming carbamate such as t-butoxycarbonyl, benzyloxycarbonyl, 9-fluorenylmethyloxycarbonyl, 2,2,2-trichloroethoxycarbonyl, and allyloxycarbonyl; protective groups forming amide such as trifluoroacetyl; protective groups forming imide such as phthaloyl; and protective groups forming sulfonamide such as p-toluenesulfonyl or 2-nitrobenzenesulfonyl.

Examples of the ketone-protective group include protective groups forming cyclic or acyclic acetal such as dimethylacetal, ethylene glycol acetal, 1,3-propanediol acetal, or dithioacetal.

Examples of the carboxyl-group-protective group include protective groups forming ester such as a methyl ester, an ethyl ester, a benzyl ester, or a t-butyl ester.

Examples of the alkynyl-group-protective group include silyl protective groups such as trimethylsilyl, triethylsilyl, t-butyldimethylsilyl, triisopropylsilyl, and t-butyldiphenylsilyl.

The reactions of the present invention will next be described in more detail.

The β-dihydrofuran derivatives represented by formula (1) and the β-tetrahydrofuran derivatives represented by formula (4), falling within the scope of the invention, are produced through the following reaction schemes.

[F12]

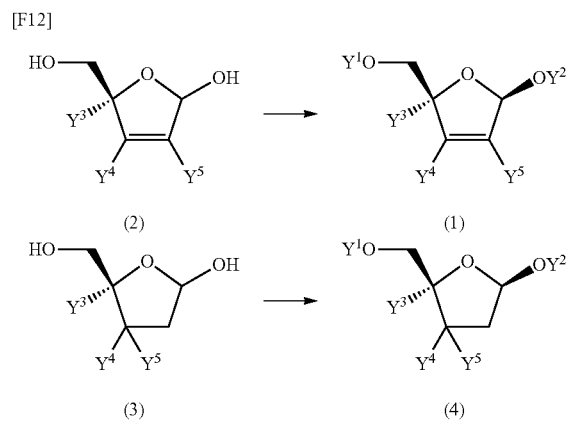

In the above reactions, a diol compound represented by formula (2) or (3) is caused to be reacted with a dialkyl dicarbonate, a diaralkyl dicarbonate, or a halide, to thereby produce a β-dihydrofuran derivatives represented by formula (1) or a β-tetrahydrofuran derivatives represented by formula (4).

The diol compound represented by formula (2) or the diol compound represented by formula (3) is generally in an equilibrium state between the 5-membered ring structure and the 6-membered ring structure. The 5-membered cyclic compound is also in an equilibrium state between the α-form and the β-form. However, even when such an equilibrium is established, a target β-form compound (i.e., a β-dihydrofuran derivative represented by formula (1) or a β-tetrahydrofuran derivative represented by formula (4)) can be produced. Thus, unless otherwise specified, these structures involved in the equilibrium are not shown in the present specification, and it is understood that any of these is equivalent to a diol compound represented by formula (2) or (3).

Examples of the dialkyl dicarbonate which may be employed in the reaction include dimethyl dicarbonate, diethyl dicarbonate, di-n-propyl dicarbonate, di-i-propyl dicarbonate, di-c-propyl dicarbonate, di-n-butyl dicarbonate, di-i-butyl dicarbonate, di-s-butyl dicarbonate, di-t-butyl dicarbonate, di-c-butyl dicarbonate, di-n-pentyl dicarbonate, di-(1-methyl-n-butyl)dicarbonate, di-(2-methyl-n-butyl)dicarbonate, di-(3-methyl-n-butyl)dicarbonate, di-(1,1-dimethyl-n-propyl)dicarbonate, di-c-pentyl dicarbonate, di-(2-methyl-c-butyl)dicarbonate, di-n-hexyl dicarbonate, di-(1-methyl-n-pentyl)dicarbonate, di-(2-methyl-n-pentyl)dicarbonate, di-(2-methyl-n-pentyl)dicarbonate, di-(1,1-dimethyl-n-butyl)dicarbonate, di-(1-ethyl-n-butyl)dicarbonate, di-(1,1,2-trimethyl-n-propyl)dicarbonate, di-c-hexyl dicarbonate, di-(1-methyl-c-pentyl)dicarbonate, di-(1-ethyl-c-butyl)dicarbonate, di-(1,2-dimethyl-c-butyl)dicarbonate, di-n-heptyl dicarbonate, di-n-octyl dicarbonate, di-n-nonyl dicarbonate, and di-n-decyl dicarbonate.

Examples of the diaralkyl dicarbonate include dibenzyl dicarbonate, di-1-phenethyl dicarbonate, and di-2-phenethyl dicarbonate.

Examples of the halide include methoxycarbonyl chloride, ethoxycarbonyl chloride, n-propoxycarbonyl chloride, i-propoxycarbonyl chloride, c-propoxycarbonyl chloride, n-butoxycarbonyl chloride, i-butoxycarbonyl chloride, s-butoxycarbonyl chloride, t-butoxycarbonyl chloride, c-butoxycarbonyl chloride, n-pentyloxycarbonyl chloride, 1-methyl-n-butoxycarbonyl chloride, 2-methyl-n-butoxycarbonyl chloride, 3-methyl-n-butoxycarbonyl chloride, 1,1-dimethyl-n-propoxycarbonyl chloride, c-pentyloxycarbonyl chloride, 2-methyl-c-butoxycarbonyl chloride, n-hexyloxycarbonyl chloride, 1-methyl-n-pentyloxycarbonyl chloride, 2-methyl-n-pentyloxycarbonyl chloride, 1,1-dimethyl-n-butoxycarbonyl chloride, 1-ethyl-n-butoxycarbonyl chloride, 1,1,2-trimethyl-n-propoxycarbonyl chloride, c-hexyloxycarbonyl chloride, 1-methyl-c-pentyloxycarbonyl chloride, 1-ethyl-c-butoxycarbonyl chloride, 1,2-dimethyl-c-butoxycarbonyl chloride, n-heptyloxycarbonyl chloride, n-octyloxycarbonyl chloride, n-nonyloxycarbonyl chloride, n-decyloxycarbonyl chloride, benzyloxycarbonyl chloride, 1-phenethyloxycarbonyl chloride, 2-phenethyloxycarbonyl chloride, methylaminocarbonyl chloride, ethylaminocarbonyl chloride, n-propylaminocarbonyl chloride, i-propylaminocarbonyl chloride, c-propylaminocarbonyl chloride, n-butylaminocarbonyl chloride, i-butylaminocarbonyl chloride, s-butylaminocarbonyl chloride, t-butylaminocarbonyl chloride, c-butylaminocarbonyl chloride, n-pentylaminocarbonyl chloride, n-heptylaminocarbonyl chloride, n-octylaminocarbonyl chloride, n-nonylaminocarbonyl chloride, n-decylaminocarbonyl chloride, dimethylaminocarbonyl chloride, diethylaminocarbonyl chloride, di-n-propylaminocarbonyl chloride, di-i-propylaminocarbonyl chloride, di-c-propylaminocarbonyl chloride, di-n-butylaminocarbonyl chloride, di-i-butylaminocarbonyl chloride, di-s-butylaminocarbonyl chloride, di-c-butylaminocarbonyl chloride, di-n-pentylaminocarbonyl chloride, di-n-heptylaminocarbonyl chloride, di-n-octylaminocarbonyl chloride, di-n-nonylaminocarbonyl chloride, di-n-decylaminocarbonyl chloride, methylethylaminocarbonyl chloride, methyl-n-propylaminocarbonyl chloride, methyl-n-butylaminocarbonyl chloride, dimethylphosphoryl chloride, diethylphosphoryl chloride, di-n-propylphosphoryl chloride, di-i-propylphosphoryl chloride, di-c-propylphosphoryl chloride, di-n-butylphosphoryl chloride, di-i-butylphosphoryl chloride, di-s-butylphosphoryl chloride, di-t-butylphosphoryl chloride, di-c-butylphosphoryl chloride, di-n-pentylphosphoryl chloride, di-(1-methyl-n-butyl)phosphoryl chloride, di-(2-methyl-n-butyl)phosphoryl chloride, di-(3-methyl-n-butyl)phosphoryl chloride, di-(1,1-dimethyl-n-propyl)phosphoryl chloride, di-c-pentylphosphoryl chloride, di-(2-methyl-c-butyl)phosphoryl chloride, di-n-hexylphosphoryl chloride, di-(1-methyl-n-pentyl)phosphoryl chloride, di-(2-methyl-n-pentyl)phosphoryl chloride, di-(1,1-dimethyl-n-butyl)phosphoryl chloride, di-(1-ethyl-n-butyl)phosphoryl chloride, di-(1,1,2-trimethyl-n-propyl)phosphoryl chloride, di-c-hexylphosphoryl chloride, di-(1-methyl-c-pentyl)phosphoryl chloride, di-(1-ethyl-c-butyl)phosphoryl chloride, di-(1,2-dimethyl-c-butyl)phosphoryl chloride, diphenylphosphoryl chloride, di-o-methylphenylphosphoryl chloride, di-m-methylphenylphosphoryl chloride, di-p-methylphenylphosphoryl chloride, di-o-trifluoromethylphenylphosphoryl chloride, di-m-trifluoromethylphenylphosphoryl chloride, di-p-trifluoromethylphenylphosphoryl chloride, di-p-ethylphenylphosphoryl chloride, di-p-i-propylphenylphosphoryl chloride, di-p-t-butylphenylphosphoryl chloride, di-o-chlorophenylphosphoryl chloride, di-m-chlorophenylphosphoryl chloride, di-p-chlorophenylphosphoryl chloride, di-o-bromophenylphosphoryl chloride, di-m-bromophenylphosphoryl chloride, di-p- bromophenylphosphoryl chloride, di-o-fluorophenylphosphoryl chloride, di-p-fluorophenylphosphoryl chloride, di-o-methoxyphenylphosphoryl chloride, di-p-methoxyphenylphosphoryl chloride, di-o-trifluoromethoxyphenylphosphoryl chloride, di-p-trifluoromethoxyphenylphosphoryl chloride, di-p-nitrophenylphosphoryl chloride, di-p-cyanophenylphosphoryl chloride, di-3,5-dimethylphenylphosphoryl chloride, di-3,5-bistrifluoromethylphenylphosphoryl chloride, di-3,5-dimethoxyphenylphosphoryl chloride, di-3,5-bistrifluoromethoxyphenylphosphoryl chloride, di-3,5-diethylphenylphosphoryl chloride, di-3,5-di-i-propylphenylphosphoryl chloride, di-3,5-dichlorophenylphosphoryl chloride, di-3,5-dibromophenylphosphoryl chloride, di-3,5-difluorophenylphosphoryl chloride, di-3,5-dinitrophenylphosphoryl chloride, di-3,5-dicyanophenylphosphoryl chloride, di-2,4,6-trimethylphenylphosphoryl chloride, di-2,4,6-tristrifluoromethylphenylphosphoryl chloride, di-2,4,6-trimethoxyphenylphosphoryl chloride, di-2,4,6-tristrifluoromethoxyphenylphosphoryl chloride, di-2,4,6-trichlorophenylphosphoryl chloride, di-2,4,6-tribromophenylphosphoryl chloride, di-2,4,6-trifluorophenylphosphoryl chloride, di-α-naphthylphosphoryl chloride, di-β-naphthylphosphoryl chloride, di-o-biphenylylphosphoryl chloride, di-m-biphenylylphosphoryl chloride, and di-p-biphenylylphosphoryl chloride.

The dialkyl dicarbonate, diaralkyl dicarbonate, or halide may be used in an amount of about 1.0 to about 3.0 eqv. by mole with respect to 1.0 eqv. by mole of the diol compound represented by formula (2) or (3), preferably 2.0 to 2.5 eqv. by mole.

The aforementioned dialkyl dicarbonates, diaralkyl dicarbonates, and halides may be used singly or in combination. The dialkyl dicarbonates, diaralkyl dicarbonates, and halides may be used in combination with an acylating agent. In this case, preferably, the diol compound represented by formula (2) or (3) reacts with the dialkyl dicarbonate, diaralkyl dicarbonate, or halide in an amount of 1.0 to 1.5 eqv. by mole with respect to 1.0 eqv. by mole of the diol compound represented by formula (2) or (3) and then with the acylating agent.

To the aforementioned reaction systems, an optional base may be added. Examples of the base include inorganic bases such as sodium hydroxide, potassium hydroxide, sodium carbonate, potassium carbonate, cesium carbonate, sodium hydrogencarbonate, potassium hydrogencarbonate, and sodium hydride; organic bases such as pyridine, 4-dimethylaminopyridine, triethylamine, tributylamine, N,N-dimethylaniline, and 1,8-diazabicyclo[5.4.0]-7-undecene; organic lithiums such as butyllithium and s-butyllithium; organic lithiumamides such as lithiumdiisopropylamide and lithium-bis(trimethylsilyl)amide; and metal alkoxides such as sodium methoxide, sodium ethoxide, and potassium t-butoxide. Of these, bases such as 4-dimethylaminopyridine, pyridine, and triethylamine are preferred.

The base may be used in an amount of about 0 to about 10 eqv. by mole with respect to 1.0 eqv. by mole of the diol compound represented by formula (2) or (3), preferably in an amount of 0 to 3 eqv. by mole.

No particular limitation is imposed on the reaction solvent, so long as it is stable under the aforementioned reaction conditions and is sufficiently inert so as not to impede reaction. Examples of the solvent include ethers such as diethyl ether, methyl t-butyl ether, tetrahydrofuran, diethyl ether, dimethoxymethane, diethoxymethane, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, 1,4-dioxane, and anisole; ketones such as acetone, methyl ethyl ketone, diethyl ketone, 2-pentanone, methyl isobutyl ketone, and cyclohexanone; aliphatic hydrocarbons such as pentane, hexane, cyclohexane, methylcyclohexane, heptane, octane, and decane; halohydrocarbons such as dichloromethane, chloroform, tetrachlorocarbon, dichloroethane, and tetrachloroethylene; aromatic hydrocarbons such as benzene, toluene, xylene, chlorobenzene, o-dichlorobenzene, m-dichlorobenzene, p-dichlorobenzene, nitrobenzene, and tetrahydronaphthalene; nitriles such as acetonitrile and propionitrile; esters such as methyl acetate, ethyl acetate, butyl acetate, and ethyl propionate; amides such as N,N-dimethylformamide, N,N-dimethylacetamide, and N-methylpyrrolidone; ureas such as 1,3-dimethylimidazolidinone and N,N,N',N'-tetramethylurea; and pyridines such as pyridine, 2-picoline, 3-picoline, 4-picoline, and 5-ethyl-2-picoline. These solvents may be used singly or in combination. Of these, halohydrocarbons are preferred, with dichloromethane being more preferred.

The reaction may be carried out in a wide temperature range. However, when economic factors including the amount(s) of reagent(s) used in the reaction are taken into consideration, generally, the reaction temperature is preferably −80 to 100° C., particularly preferably −20 to 50° C. Alternatively, the reaction may be performed at room temperature.

The reaction time (i.e., the time required for terminating the reaction), which varies depending on the amount of reactant used in the reaction, reactant concentration, reaction temperature, etc., is generally 0.1 to 20 hours, preferably 0.5 to 10 hours.

The reaction may be carried out in a batch manner or in a continuous manner. The reaction format may be chosen depending on the substrate concentration, percent conversion, productivity, etc. required for the reaction.

After completion of reaction, the solvent remaining in the reaction system is evaporated in accordance with needs, and the reaction mixture is distilled, to thereby directly yield a target product. Alternatively, the crude reaction product is sufficiently washed with water and a solvent which is not dissolved in water, and the obtained organic layer is subjected to a routine work-up process such as distillation or column chromatography, to thereby purify and isolate a β-glycoside compound.

The β-glycoside compound of the present invention represented by formula (5) is produced through the following reaction scheme.

[F13]

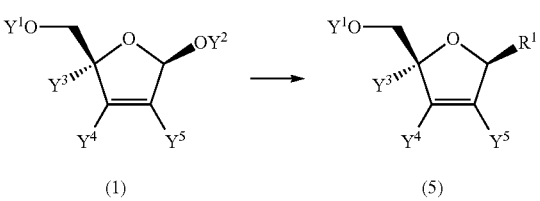

In the above reaction, a transition metal catalyst and a nucleophile are caused to act on a β-dihydrofuran derivative represented by formula (1), to thereby produce a β-glycoside compound represented by formula (5).

The metallic catalyst which may be employed in the present invention is preferably a transition metal catalyst, particularly preferably a metallic catalyst selected from among an iron catalyst, a nickel catalyst, a ruthenium catalyst, a rhodium catalyst, a palladium catalyst, an iridium catalyst, a molybdenum catalyst, a tungsten catalyst, and a platinum catalyst.

Examples of the catalyst which may be employed in the reaction are as follows.

Examples of the iron catalyst include iron complex catalysts such as pentacarbonyliron, enneacarbonyldiiron, dodecacarbonyltriiron, dichlorobis(triphenylphosphine)iron, tetracarbonyl(triphenylphosphine)iron, tricarbonylbis(triphenylphosphine)iron, sodium cyclopentadienyldicarbonylferrate, cyclopentadienyldicarbonyliron dimer, pentamethylcyclopentadienyldicarbonyliron dimer, cyclopentadienetricarbonyliron, cyclohexadienetricarbonyliron, butadienetricarbonyliron, sodium tetracarbonylferrate, bis(cyclopentadienyl)iron (ferrocene), bis(tetramethylcyclopentadienyl)iron, bis(methylcyclopentadienyl)iron(1,1'-dimethylferrocene), sodium tricarbonyl(nitroso)ferrate, tetrabutylammonium tricarbonyl(nitrosyl)ferrate, acetylferrocene, and acetylacetonatoiron.

Examples of the nickel catalyst include solid and supported nickel catalysts such as nickel-on-silica, nickel-on-alumina, and nickel-on-carbon; and nickel complex catalysts such as tetracarbonylnickel, dichlorobis(triphenylphosphine)nickel, tetrakis(triphenylphosphine)nickel, tetrakis(triphenylphosphite)nickel, bis(cyclooctadienyl)nickel, and dichloro(diphenylphosphinoethylene)nickel.

Examples of the ruthenium catalyst include supported ruthenium catalysts such as ruthenium-on-silica, ruthenium-on-alumina, and ruthenium-on-carbon; ruthenium complex catalysts such as pentacarbonylruthenium, dodecacarbonyltriruthenium, tetrahydrododecacarbonyltetraruthenium, dihydrido(dinitrogen)tris(triphenylphosphine)ruthenium, dicarbonyltris(triphenylphosphine)ruthenium, tetracarbonyl(trimethylphosphite)ruthenium, pentakis(trimethylphosphite)ruthenium, tris(acetylacetonato)ruthenium, diacetatodicarbonylbis(triphenylphosphine)ruthenium, dichlorobis(chlorotricarbonyl)ruthenium, carbonylchlorohydridotris(triphenylphosphine)ruthenium, tetrahydridotris(triphenylphosphine)ruthenium, acetatohydridotris(triphenylphosphine)ruthenium, dichlorobis(acetonitrile)bis(triphenylphosphine)ruthenium, ruthenocene, bis(pentamethylcyclopentadienyl)ruthenium, dichloro(pentamethylcyclopentadienyl)ruthenium, chloro(cyclopentadienyl)bis(triphenylphosphine)ruthenium, hydrido(cyclopentadienyl)bis(triphenylphosphine)ruthenium, chlorocarbonyl(cyclopentadienyl)ruthenium, hydrido(cyclopentadienyl)(1,5-cyclooctadiene)ruthenium, chloro(cyclopentadienyl)(1,5-cyclooctadiene)ruthenium, dihydridotetrakis(triphenylphosphine)ruthenium, cyclooctatriene(cyclooctadiene)ruthenium, chlorohydridotris(triphenylphosphine)ruthenium, tricarbonylbis(triphenylphosphine)ruthenium, tricarbonyl(cyclootcatetraene)ruthenium, tricarbonyl(1,5-cyclooctadiene)ruthenium, and dichlorotris(triphenylphosphine)ruthenium; and other ruthenium catalysts such as ruthenium chloride, ruthenium oxide, and ruthenium black.

Examples of the palladium catalyst include solid and supported palladium catalysts such as metallic palladium, palladium black, a palladium-on-silica catalyst, a palladium-on-alumina catalyst, a palladium-on-carbon catalyst, a palladium-on-barium sulfate catalyst, a palladium-on-zeolite catalyst, a palladium-on-silica.alumina catalyst, and a palladium-on-polymer catalyst; palladium complex catalysts such as dichlorobis(triphenylphosphine)palladium, dichlorobis(trimethylphosphine)palladium, dichlorobis(tributylphosphine)palladium, bis(tricyclohexylphosphine)palladium, tetrakis(triethylphosphite)palladium, bis(cycloocta-1,5-diene)palladium, tetrakis(triphenylphosphine)palladium, dicarbonylbis(triphenylphosphine)palladium, carbonyltris(triphenylphosphine)palladium, bis[1,2-bis(diphenylphosphino)ethane]palladium, bis[1,4-bis(diphenylphosphino)butane]palladium, dichloro[1,1'-bis(diphenylphosphino)ferrocene]palladium dichlorometnane complex, bis(tri-t-butylphosphine)palladium, bis(tricyclohexylphosphine)palladium, bis(triphenylphosphine)palladium acetate, dichloro[1,2-bis(diphenylphosphino)ethane]palladium, dichlorobis(tri-O-tolylphosphine)palladium, dimethylbis(diphenylmethylphosphine)palladium, dibromobis(tri-t-butylphosphino)dipalladium, tridichlorodiaminepalladium, dichlorobis(acetonitrile)palladium, tetrakis(acetonitrile)palladium tetrafluoroborate, dichlorobis(benzonitrile)palladium, dichloro(1,5-cyclooctadiene)palladium, allylpalladium chloride dimer, bis(2-methylallyl)palladium chloride dimer, bis(dibenzylideneacetone)palladium, tris(dibenzylideneacetone)(chloroform)dipalladium, tris(dibenzylideneacetone)dipalladium, acetylacetonepalladium, 2,4-pentadionepalladium, hexafluoropentadionepalladium, palladium acetate, palladium trifluoroacetate, and palladium trifluoromethanesulfonate; and other palladium catalysts such as palladium chloride and palladium oxide.

Examples of the rhodium catalyst include supported rhodium catalysts such as a rhodium-on-silica catalyst, a rhodium-on-alumina catalyst, and a rhodium-on-carbon catalyst; rhodium complex catalysts such as chlorotris(triphenylphosphine)rhodium, hexadecacarbonylhexarhodium, dodecacarbonyltetrarhodium, dichlorotetracarbonyldirhodium, hydridotetracarbonylrhodium, hydridocarbonyltris(triphenylphosphine)rhodium, hydridotetrakis(triphenylphosphine)rhodium, dichlorobis(cyclooctadiene)dirhodium, dicarbonyl(pentamethylcyclopentadienyl)rhodium, cyclopentadienylbis(triphenylphosphine)rhodium, and dichlorotetrakis(aryl)dirhodium; and other rhodium catalysts such as rhodium chloride and rhodium oxide.

Examples of the iridium catalyst include iridium complex catalysts such as chloro(cyclooctadienyl)iridium dimer.

Examples of the molybdenum catalyst include molybdenum complex catalysts such as hexacarbonylmolybdenum, biscarbonyltetra(isocyano)molybdenum, tricarbonyltris(acetonitrile)molybdenum, pentacarbonylbis(trifluoromethanesulfonyl)molybdenum, dibromotetracarbonylmolybdenum dimer, chlorotetracarbonylbis(acetonitrile)-(trichlorostannyl)molybdenum, tetracarbonyl(bipyridyl)molybdenum, tricarbonyl(bipyridyl)(acetonitrile)molybdenum, and (N,N'-bis(cyclohexyl)ethylenediimine)tetracarbonylmolybdenum.

Examples of the tungsten catalyst include tungsten complex catalysts such as tetracarbonyltetra(acetonitrile)tungsten, pentacarbonylbis(trifluoromethanesulfonyl)tungsten, and dibromotetracarbonyltungsten dimer.

Examples of the platinum catalyst include supported platinum catalysts such as a platinum-on-silica catalyst, a platinum-on-alumina catalyst, and a platinum-on-carbon catalyst; platinum complex catalysts such as dichlorobis(triphenylphosphine)platinum, dichlorobis(trimethylphosphine)platinum, dichlorobis(tributylphosphine)platinum, tetrakis(triphenylphosphine)platinum, tetrakis(triphenylphosphite)platinum, tris(triphenylphosphine)platinum, dicarbonylbis(triphenylphosphine)platinum, carbonyltris(triphenylphosphine)platinum, cis-bis(benzonitrile)

dichloroplatinum, bis(1,5-cyclooctadiene)platinum, and methylenebis(triphenylphosphine)platinum; and other platinum catalysts such as platinum chloride, platinum oxide (Adams catalyst), and platinum black.

Among these metallic catalysts, a nickel catalyst, a palladium catalyst, a ruthenium catalyst, and a rhodium catalyst are preferred. A complex catalyst is a suitably employed form of the catalyst.

These catalysts may be used singly or in combination.

The amount of transition metal catalyst used in the reaction is generally 0.0001 to 50 mol % with respect to the β-dihydrofuran derivative represented by formula (1), preferably 0.001 to 20 mol %.

In accordance with needs, a ligand may be added to the aforementioned catalyst. Examples of the ligand include monodentate and polydentate tertiary phosphines such as trimethylphosphine, triethylphosphine, tributylphosphine, triphenylphosphine, tris(p-tolyl)phosphine, tris(2,6-dimethylphenyl)phosphine, sodium diphenylphosphinobenzene-3-sulfonate, bis(3-sulfonatophenyl)phosphinobenzene sodium salt, tri(2-furyl)phosphine, bis(diphenylphosphino)methane, 1,2-bis(diphenylphosphino)ethane, 1,3-bis(diphenylphosphino)propane, 1,4-bis(diphenylphosphino)butane, 2,3-bis(diphenylphosphino)butane, 2,4-bis(diphenylphosphino)pentane, 1,1'-bis(diphenylphosphino)ferrocene, 1,3-bis(diisopropylphosphino)propane, 2,2'-bis(diphenylphosphino)biphenyl, 4,5-bis[(diphenylphosphinyl)methyl]-2,2-dimethyl[1,3]dioxolane, 1,2-bis(O-anisylphenylphosphino)ethane, 2,2'-bis(diphenylphosphino)-1,1'-binaphthyl, Trost ligand, tris(3-sulfonatophenyl)phosphine sodium salt; phosphorous acid esters such as trimethyl phosphite, triethyl phosphite, tripropyl phosphite, tributyl phosphite, triphenyl phosphite, and tris(2,6-dimethylphenyl)phosphite; phosphonium salts such as triphenylmethylphosphonium iodide, triphenylmethylphosphonium bromide, triphenylmethylphosphonium chloride, triphenylallylphosphonium iodide, triphenylallylphosphonium bromide, triphenylallylphosphonium chloride, tetraphenylphosphonium iodide, tetraphenylphosphonium bromide, and tetraphenylphosphonium chloride; phosphoric acid esters such as triphenyl phosphate, trimethyl phosphate, triethyl phosphate, and triallyl phosphate; organic arsines such as triphenylarsine; nitriles such as benzonitrile and acetonitrile; ketones such as acetylacetone; dienes such as cyclopentadiene, pentamethylcyclopentadiene, and 1,5-cyclooctadiene; azo heterocyclic system ligands such as pyridine, 2-picoline, 3-picoline, 4-picoline, 2,2-bipyridyl, terpyridine, 1,10-phenanthroline, 8-hydroxyquinoline, bisoxazolinylpyridine (Pybox), 1,4-dimethylpyrazole, 1,3,5-trimethylpyrazole, pyrimidine, and pyrazine; π acid ligands such as dimethyl maleate, dimethyl fumarate, phenylacetylene, and diphenylacetylene; reaction atmosphere gas such as carbon monoxide; and N-heterocyclic carbenes such as 1,3-bis(2,6-diisopropylphenyl)imidazolium chloride.

When a ligand is added, the amount thereof is generally 0.1 to 10,000 mol % with respect to transition metal catalyst, preferably 1 to 5,000 mol %.

To the aforementioned reaction systems, an optional base may be added. Examples of the base include inorganic bases such as sodium hydroxide, potassium hydroxide, sodium carbonate, potassium carbonate, cesium carbonate, sodium hydrogencarbonate, potassium hydrogencarbonate, and sodium hydride; organic bases such as pyridine, 4-dimethylaminopyridine, triethylamine, tributylamine, N,N-dimethylaniline, and 1,8-diazabicyclo[5.4.0]-7-undecene; organic lithiums such as butyllithium and s-butyllithium; organic lithiumamides such as lithiumdiisopropylamide and lithium-bis(trimethylsilyl)amide; and metal alkoxides such as sodium methoxide, sodium ethoxide, and potassium t-butoxide.

Among them, bases such as sodium carbonate, potassium carbonate, sodium hydrogencarbonate, triethylamine, and sodium hydride are preferred, with sodium hydride being more preferred.

The base may be used in an amount of about 0 to about 10 eqv. by mole with respect to 1.0 eqv. by mole of the β-dihydrofuran derivative represented by formula (1), preferably 0 to 2 eqv. by mole.

Examples of the nucleophile which may be employed in the reaction include heterocyclic bases such as optionally substituted uracils, optionally protected thymines (e.g., 4-O-methylthymine), cytosine, imidazole, benzimidazole, benzotriazole, optionally substituted thiouracils, and purines. Among them, preferred are optionally substituted uracil, optionally protected thymine, cytosine, imidazole, benzimidazole, benzotriazole, optionally substituted thiouracil, optionally substituted purine. Through increasing the amount of nucleophile, the β-form compound can be produced at higher yield.

In order to attain smooth reaction, the nucleophile may be siliyalted in advance with a silylating reagent such as chlorotrimethylsilane or bistrimethylsilylacetamide.

Preferably, the reaction is performed under solvent-diluted conditions for smoothly performing the reaction including sufficient mixing and dispersing the reagents used in the reaction. No particular limitation is imposed on the solvent employed in the reaction, so long as the solvent is inert to the reaction. Examples of the solvent include ethers such as diethyl ether, methyl t-butyl ether, tetrahydrofuran, diethyl ether, dimethoxymethane, diethoxymethane, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, 1,4-dioxane, and anisole; alcohols such as methanol, ethanol, 1-propanol, 2-propanol, 1-butanol, 2-butanol, isobutanol, 2-methyl-2-propanol, methyl cellosolve, ethyl cellosolve, i-propyl cellosolve, diethylene glycol monomethyl ether, diethylene glycol monoethyl ether, diethylene glycol monobutyl ether, cyclohexanol, and benzyl alcohol; ketones such as acetone, methyl ethyl ketone, diethyl ketone, 2-pentanone, methyl isobutyl ketone, and cyclohexanone; aliphatic hydrocarbons such as pentane, hexane, cyclohexane, methylcyclohexane, heptane, octane, and decane; halohydrocarbons such as chloroform, tetrachlorocarbon, dichloroethane, and tetrachloroethylene; aromatic hydrocarbons such as benzene, toluene, xylene, chlorobenzene, o-dichlorobenzene, m-dichlorobenzene, p-dichlorobenzene, nitrobenzene, and tetrahydronaphthalene; nitriles such as acetonitrile and propionitrile; esters such as methyl acetate, ethyl acetate, butyl acetate, and ethyl propionate; amides such as N,N-dimethylformamide, N,N-dimethylacetamide, and N-methylpyrrolidone; ureas such as 1,3-dimethylimidazolidinone and N,N,N',N'-tetramethylurea; pyridines such as pyridine, 2-picoline, 3-picoline, 4-picoline, and 5-ethyl-2-picoline; and water. These solvents may be used singly or in combination.

The reaction may be carried out in a wide temperature range. However, when economic factors including the amount(s) of reagent(s) used in the reaction are taken into consideration, generally, the reaction temperature is preferably −80 to 100° C., particularly preferably −20 to 50° C. Alternatively, the reaction may be performed at room temperature.

The reaction time (i.e., the time required for terminating the reaction), which varies depending on the amount of reactant used in the reaction, reactant concentration, reaction temperature, etc., is generally 0.1 to 20 hours, preferably 0.5 to 10 hours.

The reaction may be carried out in a batch manner or in a continuous manner. The reaction format may be chosen depending on the substrate concentration, percent conversion, productivity, etc. required for the reaction.

After completion of reaction, the solvent remaining in the reaction system is evaporated in accordance with needs, and the reaction mixture is distilled, to thereby directly yield a target product. Alternatively, the crude reaction product is sufficiently washed with water and a solvent which is not dissolved in water, and the obtained organic layer is subjected to a routine work-up process such as distillation or column chromatography, to thereby purify and isolate a β-glycoside compound.

Next, 4'-ethynyl d4T and an analog thereof, which are represented by formula (7), are produced through the following reaction scheme.

[F14]

(5)            (7)

In the above reaction, a β-glycoside compound represented by formula (5) is deprotected, to thereby form a compound represented by formula (7); i.e., 4'-ethynyl d4T or an analog thereof. As used herein, the term "deprotection" refers not only to elimination of substituent $Y^1$ but also to optional elimination of a protective group in substituent $Y^3$, $Y^4$, $Y^5$, or $R^1$. Notably, similar to the case of formula (5), in formula (7), an isomer having a substituent $R^{1'}$ on the lower side of the sheet is called an α-form, and another isomer having a substituent $R^{1'}$ on the upper side of the sheet is called a β-form, when —$CH_2$—OH is fixed on the upper side of the sheet.

The deprotection reaction may be performed through a known technique; for example, a method disclosed in Greene and Wuts, "Protective Groups in Organic Synthesis (Fourth Edition)."

EXAMPLES

The present invention will next be described in detail by way of examples, which should not be construed as limiting the invention thereto. Needless to say, those skilled in the art may carry out the steps with appropriate modification based on common technical knowledge in the art.

$^1$H-NMR and LC were measured by means of the following apparatuses under the following conditions (NMR: nuclear magnetic resonance spectrometry, LC: liquid chromatography). Stereochemistry (β/α ratio) was determined from the HPLC peak area ratio.

[1] $^1$H-NMR
Apparatus: JNM-ECP300 (product of JEOL) (300 MHz)
Solvent: $CDCl_3$, $CD_3OD$
[2] LC
Exemplary LC measurement conditions:
  Column: Capcellpak C18 MGII 4.6×100 mm 3 μm
  Oven Temp: 40° C.
  Eluent: $CH_3CN$, $H_2O$
  $CH_3CN$=20% (0 min)→80% (15 min)
  Flow rate: 1.2 mL/min
  Detector: UV 254 nm Referential Example 1

Production of (5R)-2-hydroxy-5-hydroxymethyl-5-(2-trimethylsilylethynyl)-2,5-dihydrofuran Tetrahydrofuran (2,700 mL) and water (300 mL) were added to a glass reactor with a nitrogen atmosphere and stirred. Sodium hydrogencarbonate (343 g) and sodium acetate (167 g) were added to the reactor. The reaction mixture was cooled to −15° C., and N-bromosuccinimide (376 g) and furfuryl alcohol (200 g) were added dropwise thereto, followed by mixing at −15° C. for 10 minutes. Subsequently, 4-dimethylaminopyridine (50 g) and acetic anhydride (416 g) were added to the mixture. The resultant mixture was warmed to room temperature and stirred for 3 hours. This reaction mixture was cooled to 5° C. or lower, and the pH of the mixture was adjusted to 6.5 through addition of 10N aqueous sodium hydroxide (200 mL) and 2N sodium hydroxide (760 mL). Ethyl acetate (1,500 mL) was added thereto under stirring, and saturated aqueous sodium hydrogencarbonate (1,500 mL) was added to the thus-separated organic layer under stirring, for phase separation. The organic layer was concentrated under reduced pressure, to thereby yield 279 g of 2-acetyloxy-5,6-dihydro-2H-pyrano-5-one (yield: 73%).

2-Acetyloxy-5,6-dihydro-2H-pyrano-5-one (150 g) and 2-propanol (3,000 mL) were added to a glass reactor, and the reaction mixture was heated to 30° C. An aqueous solution of Lipase PS Amano SD (trade name, product of Amano Enzyme Co., Ltd.) (15 g) dissolved in water (300 mL) was added dropwise to the reaction mixture, and stirring was performed for 2.5 hours. The thus-obtained reaction mixture was filtered, and the filtrate was concentrated under reduced pressure. Subsequently, water (350 mL) and toluene (750 mL) were added to the residue, and the mixture was stirred for phase separation. Saturated aqueous sodium hydrogencarbonate (350 mL) was added to the thus-separated organic layer under stirring, for phase separation. Saturated aqueous sodium hydrogencarbonate (350 mL) was added to the thus-separated organic layer under stirring, for phase separation. The organic layer was concentrated under reduced pressure, to thereby yield 27 g of (R)-2-acetyloxy-5,6-dihydro-2H-pyrano-5-one (yield: 18%).

Dehydrated tetrahydrofuran (440 mL) and trimethylsilylacetylene (47 g) were added to a glass reactor with a nitrogen atmosphere and stirred, and the mixture was cooled to −30° C. Separately, a solution (310 mL) of 1.57-mol/L n-butyllithium in hexane was prepared, and (R)-2-acetyloxy-5,6-dihydro-2H-pyrano-5-one (62 g) was dissolved in dehydrated tetrahydrofuran (437 mL). Then, the two solutions were added dropwise to the mixture, followed by stirring for 30 minutes. The resultant mixture was warmed to room temperature, and a mixture of acetic acid (34 g) and tetrahydrofuran (174 mL) and water (300 mL) were added thereto under stirring for phase separation. Saturated aqueous sodium hydrogencarbonate (300 mL) was added to the thus-separated organic layer under stirring, for phase separation. Then, water (300 mL) was added to the thus-separated organic layer under stirring, for phase separation. The organic layer was concentrated under reduced pressure, to thereby yield 100 g of (2R,5R)-2-acetyloxy-5,6-dihydro-2H-pyrano-5-(2-trimethylsilylethynyl)-5-ol (yield: 98%).

Acetonitrile (300 mL) and (2R,5R)-2-acetyloxy-5,6-dihydro-2H-pyrano-5-(2-trimethylsilylethynyl)-5-ol (100 g) were added to a glass reactor under stirring, and the mixture was heated to 40° C. An aqueous solution of Lipase PS Amano SD (trade name, product of Amano Enzyme Co., Ltd.) (10 g) dissolved in water (400 mL) was added dropwise to the mixture, and stirring was performed for 15 hours. The reaction mixture was cooled to 20° C., and water and ethyl acetate were added to the reaction mixture under stirring for phase separation. The thus-separated organic layer was concentrated under reduced pressure. The residue was purified through silica gel column chromatography, to thereby yield 21 g of (5R)-2-hydroxy-5-hydroxymethyl-5-(2-trimethylsilylethynyl)-2,5-dihydrofuran (yield: 25%). The ¹H-NMR data of the compound are as follows.

¹H-NMR: δH (300 MHz; CDCl₃) 5.83-6.22 (m, 3H), 3.60-4.25 (m, 2H), 0.17-0.35 (m, 9H).

Example 1

Production of (2S,5R)-5-t-butoxycarbonyloxymethyl-5-(2-trimethylsilylethynyl)-2-t-butoxycarbonyloxy-2,5-dihydrofuran represented by formula (A)

[F15]

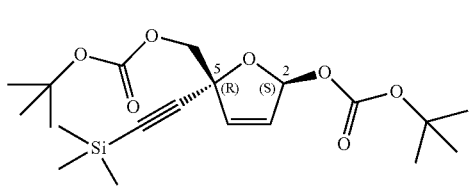

(A)

The above-produced (5R)-2-hydroxy-5-hydroxymethyl-5-(2-trimethylsilylethynyl)-2,5-dihydrofuran (2.5 g) was added to a glass reactor, and the atmosphere of the reactor was changed to nitrogen. To the reactor, dichloromethane (12.5 mL) and 4-dimethylaminopyridine (144 mg) were added under stirring, and the mixture was cooled to 0° C. To the resultant mixture, di-t-butyl dicarbonate (6.4 g) was added dropwise, and the mixture was stirred for 2 hours. Water (8 mL) was added to the reaction mixture under stirring, and the thus-separated organic layer was concentrated under reduced pressure. The residue was purified through silica gel column chromatography, to thereby yield 4.6 g of (2S,5R)-5-t-butoxycarbonyloxymethyl-5-(2-trimethylsilylethynyl)-2-t-butoxycarbonyloxy-2,5-dihydrofuran as an oil (yield: 94%, β/α=>99/1). The ¹H-NMR data of the compound are as follows.

¹H-NMR: δH (300 MHz; CDCl₃) 6.79 (m, 1H), 6.22 (dd, 1H), 5.98 (dd, 1H), 4.31 (d, 1H), 4.23 (d, 1H), 1.48 (m, 18H), 0.15 (s, 9H)

Example 2

Production of (2R,5R)-5-t-butoxycarbonyloxymethyl-5-(2-trimethylsilylethynyl)-2-(thymin-1-yl)-2,5-dihydrofuran represented by formula (B)

[F16]

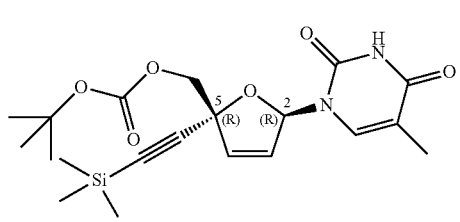

(B)

(2S,5R)-5-t-Butoxycarbonyloxymethyl-5-(2-trimethylsilylethynyl)-2-t-butoxycarbonyloxy-2,5-dihydrofuran (β/α=>99/1) (2.0 g) was added to a glass reactor, and the atmosphere of the reactor was changed to nitrogen. To the reactor, thymine (3.1 g) and N,N'-dimethylformamide (40 mL) were added under stirring. To the resultant mixture, tetrakis(triphenylphosphine)palladium(0) (560 mg) was added, and the mixture was stirred at room temperature for 30 minutes. The reaction mixture was concentrated, and the residue was purified through silica gel column chromatography, to thereby yield 1.6 g of (2R,5R)-5-t-butoxycarbonyloxymethyl-5-(2-trimethylsilylethynyl)-2-(thymin-1-yl)-2,5-dihydrofuran (yield: 78%, β/α=>99/1). The ¹H-NMR data of the compound are as follows.

¹H-NMR: δH (300 MHz; CDCl₃) 7.95 (brs, 1H), 7.45 (d, 1H), 7.15 (dd, 1H), 6.21 (dd, 1H), 5.88 (d, 1H), 4.56 (d, 1H), 4.19 (d, 1H), 1.93 (s, 3H), 1.48 (s, 9H), 0.17 (s, 9H).

Example 3

Production of 4'-ethynyl-2',3'-didehydro-3'-deoxythymidine represented by formula (C)

[F17]

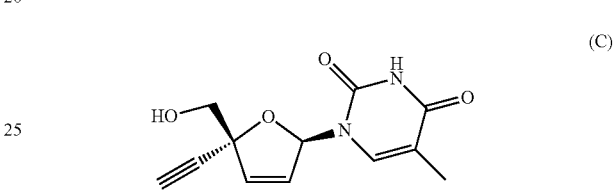

(C)

(2R,5R)-5-t-Butoxycarbonyloxymethyl-5-(2-trimethylsilylethynyl)-2-(thymin-1-yl)-2,5-dihydrofuran (35 mg) was added to a glass reactor, and the atmosphere of the reactor was changed to nitrogen. To the reactor, potassium carbonate (72 mg) and methanol (3.5 mL) were added, and the mixture was stirred at room temperature for 18 hours. The reaction mixture was mixed with water and acetonitrile so as to form a uniform solution, and the solution was quantitated (LC). The yielded compound was found to be 4'-ethynyl-2',3'-didehydro-3'-deoxythymidine (yield: 94%, calculated through quantitation) (internal standard: methyl phthalate). The ¹H-NMR data of the compound are as follows.

¹H-NMR: δH (300 MHz; CD₃OD) 7.71 (s, 1H), 7.03 (m, 1H), 6.32 (dd, 1H), 6.00 (dd, 1H), 3.82 (d, 1H), 3.75 (d, 1H), 3.08 (s, 1H), 1.82 (s, 3H).

Example 4

Production of (2S,5R)-5-t-butoxycarbonyloxymethyl-5-ethynyl-2-t-butoxycarbonyloxy-2,5-dihydrofuran represented by formula (D)

[F18]

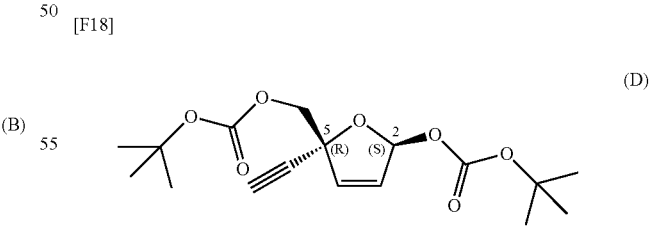

(D)

(5R)-2-Hydroxy-5-hydroxymethyl-5-(2-trimethylsilylethynyl)-2,5-dihydrofuran (620.5 g) was dissolved in toluene (3 kg). The solution was added to a glass reactor under nitrogen and cooled to 2° C. To the reactor, 4-dimethylaminopyridine (17.9 g) was added under stirring. Then, di-t-butyl dicarbonate (1.9 kg) was added dropwise, and the mixture was stirred for 20 minutes. To the reaction mixture, methanol (5.6 kg) and potassium fluoride (347 g) were added, and the mixture was stirred for 4 hours. Then, water was added thereto under stirring for phase separation, to thereby recover an organic layer. A portion (11/20 amount) of the organic layer was taken and concentrated, and the residue was purified through recrystallization from ethanol and heptane, to thereby yield 331 g of (2S,5R)-5-t-butoxycarbonyloxymethyl-5-ethynyl-2-t-butoxycarbonyloxy-2,5-dihydrofuran (yield: 61%, β/α=>99/1). The $^1$H-NMR data of the compound are as follows.

$^1$H-NMR: δH (300 MHz; CDCl$_3$) 6.80 (m, 1H), 6.26 (dd, 1H), 6.00 (dd, 1H), 4.31 (d, 1H), 4.23 (d, 1H), 2.60 (s, 1H), 1.49 (m, 18H).

Example 5

Production of (2R,5R)-5-t-butoxycarbonyloxymethyl-5-ethynyl-2-(thymin-1-yl)-2,5-dihydrofuran represented by formula (E)

[F19]

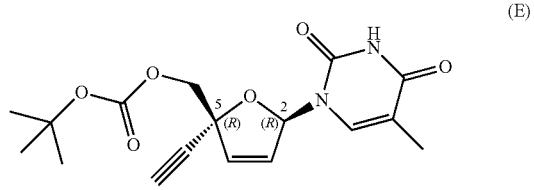

(E)

Thymine (16.7 g), N,N'-dimethylformamide (162 g), and tetrakis(triphenylphosphine)palladium(0) (917 mg) were added to a glass reactor under nitrogen, and the mixture was heated to 55° C. Then, a solution of (2S,5R)-5-t-butoxycarbonyloxymethyl-5-ethynyl-2-t-butoxycarbonyloxy-2,5-dihydrofuran (β/α=>99/1) (9.0 g) in N,N'-dimethylformamide was added dropwise thereto, and the mixture was stirred for 30 minutes. The reaction mixture was filtered, and water was added to the filtrate, followed by stirring for phase separation. The thus-separated organic layer was concentrated. The residue was purified through recrystallization from acetonitrile and toluene, to thereby yield 6.5 g of (2R,5R)-5-t-butoxycarbonyloxymethyl-5-ethynyl-2-(thymin-1-yl)-2,5-dihydrofuran (yield: 72%, β/α=>99/1). The $^1$H-NMR data of the compound are as follows.

$^1$H-NMR: δH (300 MHz; CDCl$_3$) 8.47 (brs, 1H), 7.42 (d, 1H), 7.17 (dd, 1H), 6.22 (dd, 1H), 5.93 (d, 1H), 4.56 (d, 1H), 4.22 (d, 1H), 2.66 (s, 1H), 1.93 (s, 3H), 1.49 (s, 9H).

Example 6

Production of 4'-ethynyl-2',3'-didehydro-3'-deoxythymidine represented by formula (C)

[F20]

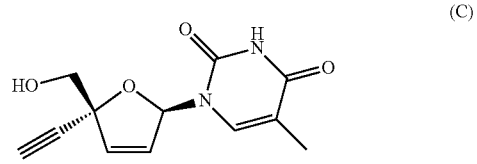

(C)

(2R,5R)-5-t-Butoxycarbonyloxymethyl-5-ethynyl-2-(thymin-1-yl)-2,5-dihydrofuran (5 g) was added to a glass reactor under nitrogen, and methanol (150 g) and potassium carbonate (9.9 g) were added. The mixture was stirred at 37° C. for 4 hours. The reaction mixture was concentrated and dissolved in water. Aqueous sodium hydroxide and toluene were added to the solution under stirring for phase separation, and hydrochloric acid and methyl ethyl ketone were added to the aqueous layer, followed by stirring for further phase separation. The thus-separated organic layer was concentrated, and the residue was purified through recrystallization from ethanol and heptane, to thereby yield 3.2 g of 4'-ethynyl-2', 3'-didehydro-3'-deoxythymidine (yield: 91%, β/α=>99/1). The $^1$H-NMR data of the compound are the same as those of the compound produced in Example 3.

INDUSTRIAL APPLICABILITY

The process of the present invention is enables large-scale synthesis, under mild conditions, of 4'-ethynyl-2',3'-didehydro-3'-deoxythymidine, which is a possible candidate of an active ingredient of a drug effective for the treatment of HIV infections, as well as analogs thereof, which are important intermediates for fine chemicals such as pharmaceuticals and agrochemicals. Thus, the process of the invention has industrial applicability.

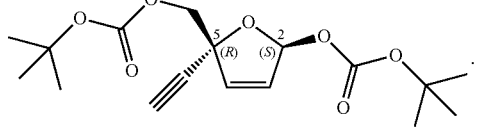

4. A β-dihydrofuran derivative according to claim 1, which is (2S,5R)-5-t-butoxycarbonyloxymethyl-5-(2-trimethylsilylethynyl)-2-t-butoxycarbonyloxy-2,5-dihydrofuran, of the formula
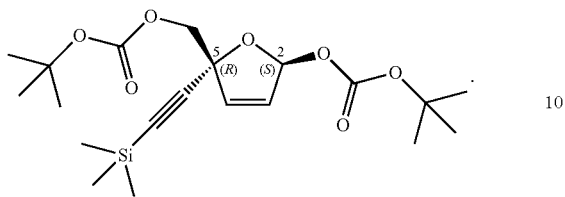

The invention claimed is:

1. A β-dihydrofuran derivative represented by formula (1):

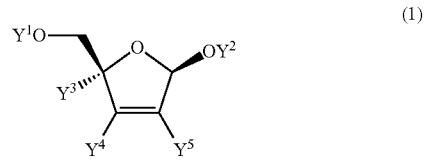

(1)

wherein
$Y^1$ represents a tertiary-butoxycarbonyl group;
$Y^2$ represents a tertiary-butoxycarbonyl group; and
$Y^3$, $Y^4$, and $Y^5$ each represent a hydrogen atom, a halogen atom, an alkyl group, an aryl group, an acyl group, an alkenyl group, an aralkyl group, a cycloalkyl group, a hydroxyl group, an alkoxy group, an aryloxy group, an aralkyloxy group, an alkylthio group, an arylthio group, an amino group, an alkylamino group, a trialkylsilyloxy group, a trisubstituted silyl group, an alkylaminocarbonyl group, a halomethyl group, an optionally protected formyl group, a C1 to C7 ester group, an optionally protected hydroxymethyl group, a vinyl group, an optionally protected alkynyl group, a cyano group, or an optionally substituted iminomethyl group.

2. A β-dihydrofuran derivative according to claim 1, wherein $Y^3$ is an optionally protected alkynyl group, and each of $Y^4$ and $Y^5$ is a hydrogen atom.

3. A β-dihydrofuran derivative according to claim 1, which is (2S,5R)-5-t-butoxycarbonyloxymethyl-5-ethynyl-2-t-butoxycarbonyloxy-2,5-dihydrofuran, of the formula